United States Patent [19]

Camiener

[11] Patent Number: 5,344,637
[45] Date of Patent: Sep. 6, 1994

[54] USE OF SATURATED, RING-CONTAINING COMPOUNDS AS CLEARING SOLVENTS IN HISTOLOGIC PROCEDURES

[76] Inventor: Gerald W. Camiener, 26700 Hurlingham Rd., Beachwood, Ohio 44122

[21] Appl. No.: 69,718

[22] Filed: Jun. 1, 1993

[51] Int. Cl.$^5$ ............................................. G01N 1/34
[52] U.S. Cl. ............................................ 424/3; 435/4
[58] Field of Search ................... 435/4; 134/40; 424/3

[56] References Cited

U.S. PATENT DOCUMENTS

| | | | |
|---|---|---|---|
| 4,244,862 | 1/1981 | Handa et al. | 260/42.47 |
| 4,257,346 | 3/1981 | Ornstein et al. | 118/641 |
| 4,430,488 | 2/1984 | Zboril | 526/84 |
| 4,925,497 | 5/1990 | Thierheimer, Jr. | 134/40 |
| 5,008,234 | 4/1991 | Ozin et al. | 502/326 |

OTHER PUBLICATIONS

Grant and Hackh's Chemical Dictionary p. 183 (1987).

*Primary Examiner*—Douglas W. Robinson
*Assistant Examiner*—Sandra Saucier
*Attorney, Agent, or Firm*—Wegner, Cantor, Mueller & Player

[57] ABSTRACT

A method of using saturated organic ring-containing compounds as clearing solvents for biological materials is described. The clearing solvents are equally effective or superior to conventional clearing solvents but they lack the toxic and noxious characteristics of conventional clearing solvents. The clearing solvents are used to replace the alcohol and/or other dehydrants in fixed biological materials and to remove wax from wax-imbedded biological materials.

11 Claims, No Drawings

USE OF SATURATED, RING-CONTAINING COMPOUNDS AS CLEARING SOLVENTS IN HISTOLOGIC PROCEDURES

FIELD OF THE INVENTION

The present invention is directed to the use of saturated, ring-containing compounds as clearing solvents for biological materials.

BACKGROUND OF THE INVENTION

Normal histologic procedures that are used to prepare slides bearing thin slices of tissues or other biological materials for microscopic examination require the use of so-called clearing solvents in at least two different stages of the processing:

1. To replace (dissolve away) alcohol and/or other dehydrants that are present in gross pieces of tissues immediately following tissue fixation steps. This replacing (clearing) solvent must also have the property of being readily soluble in the paraffin wax that is used in subsequent steps to "embed" the tissue.

2. To dissolve away the embedding paraffin wax that is present in the thin slices (sections) of tissue that are prepared with a microtome knife from the gross pieces (chunks) of tissues described above. The "dissolving" process must be rapid and complete, and the solvent must be easily removed by alcohol or other dehydrants that are used in subsequent washing steps.

Historically, the main solvents used for the "clearing" steps have been toluene and xylene. However, both of these solvents suffer from major problems including fire safety (relatively low flash- and boiling points) and multiple toxicities (including headaches, nausea, and damage to liver, kidneys, blood, eyes and nervous system), as well as being extremely noxious to work with in confined areas with limited air circulation like hospitals and laboratories.

In recent years, there have been numerous attempts to replace these solvents with safer and less-noxious types of clearing solvents, but these attempts largely have been unsuccessful. As a result of these unsuccessful attempts, it was generally thought that the effectiveness of solvents (for dewaxing purposes) was directly linked to their dangerous and noxious properties. That is, it was thought that the better the clearing solvent, the more dangerous and more noxious it was. The following is a brief summary of alternate clearing agents that have been used conventionally:

1. Chlorinated hydrocarbons are effective clearing solvents, but they are considered to be very toxic and noxious chemicals. Essentially, the use of all of the effective solvents has been restricted to some extent by the government.

2. Terpenes (including d-limonene, α-pinenes and dipentene) are moderately effective clearing solvents, but they too are considered toxic and reportable under OSHA. More critically, they are extremely noxious and overpowering to laboratory workers. They also tend to dry slowly and leave an oily residue.

3. Higher molecular weight paraffinic (straight-chain) and isoparaffinic (branched chain) hydrocarbon solvents generally are safer and less noxious than toluene and xylene, but they are not very good as clearing solvents. They not only dissolve wax quite slowly, as compared to xylene for example, but they also dry slowly and often leave an oily residue. Lower molecular weight paraffinic and isoparaffinic solvents have serious problems with fire safety and smell.

4. Aromatic petroleum-derived solvents generally are much more effective clearing solvents than the paraffinic and isoparaffinic materials, but they are very much more toxic and noxious. As noted above, effectiveness was generally considered to be related directly to toxicity, noxious odor, and flammability.

DETAILED DESCRIPTION OF THE INVENTION

The present invention is a result of the discovery that the effectiveness of clearing solvents can be separated from problems of toxicity and noxiousness by using saturated forms of aromatic compounds as the solvents. The present inventor has discovered that it is the "ring" structure that provides the best (most effective) kind of non-halogenated clearing solvent, and that it is the "aromaticity" (unsaturated nature) of the solvent that is associated with toxicity and noxiousness. Aromatic (less saturated) ring chemicals have higher levels of toxicity and odors; more saturated (more hydrogenated, less unsaturated) ring chemicals and distillation fractions exhibit much lower toxicities and odors.

In one embodiment, the present invention comprises a method of preparing fixed biological material for microscopic examination, comprising contacting said biological material with a clearing solvent to remove the alcohol and or other dehydrants contained in the biological material or to remove wax in the biological material following microtome sectioning, wherein the clearing solvent comprises from 5% to 100%, by weight, of a compound selected from the group consisting of unsubstituted and substituted derivatives of saturated, organic ring-containing compounds, either alone, or present in hydrogenated aromatic petroleum distillates, and in combinations thereof.

"Clearing solvent", as used herein, refers to a solution into which biological material is placed in order to remove alcohol and/or other dehydrants or to remove wax following microtome sectioning.

Preferred examples of the clearing solvent are unsubstituted and substituted derivatives of cyclopentane, cyclopentene, cyclohexane and cyclohexene. Preferred substituents are straight or branched alkyl and alkenyl groups having 1 to 10 carbon atoms and halogenated groups. Also, these clearing solvents, i.e., cyclopentane, cyclopentene, cyclohexane and cyclohexene, may be further substituted with an organic ring-containing compound selected from the group consisting of unsubstituted and substituted derivatives of cyclopentane, cyclopentene, cyclohexane and cyclohexene.

Other preferred clearing solvents are unsubstituted and substituted-derivatives of saturated forms of the bicyclic compounds biphenyl, naphthalene, quinoline, isoquinoline, diphenyl, acenaphthene, and cyclopentadiene, and the polycyclic compounds fluorene, phenanthrene, anthracene, p-terphenyl fluoranthene, pyrene and chrysene.

Also, the clearing solvents include acids derived from the compounds listed herein as clearing solvents. For example, cyclopentanecarboxylic acid, cyclopentylacetic acid, and the alkyl-and alkenyl-derivatives of cyclopentyl, cyclopentenyl, cyclohexyl and cyclohexenyl formic and acetic acids are preferred acid clearing solvents.

The clearing solvent also includes compounds with a nitrogen-and/or sulfur-containing ring. For example, unsubstituted and substituted saturated or partially-saturated quinoline, isoquinoline, pyridine, indole, acridine, carbazole, tetramethylene and pentamethylene sulfides are preferred compounds of this category.

The clearing solvent may be prepared by distilling a mixture of saturated and unsaturated organic ring-containing compounds, such as a petroleum-based mixture, and then selecting distillation fractions that have higher levels of saturation, i.e., more hydrogenated forms containing fewer double bonds than the original distillate mixture. Also, the dewaxing agent can be prepared by subjecting unsaturated organic ring-containing compounds, either alone or present in petroleum distillates, to hydrogenation.

Side-by-side comparisons with a wide variety of saturated (hydrogenated) organic ring chemicals and distillation fractions compared to their unsaturated counterparts have shown that the saturated ring-containing compounds tend to be better clearing solvents than the unsaturated materials, yet are largely free from toxic and noxious properties. Thus, toxicity and noxiousness are not linked to effectiveness, contrary to the literature.

EXAMPLES

For example, methylcyclohexane is more effective as a clearing solvent than toluene; dimethylcyclohexane is more effective than xylene; and so forth as described below in Table 1. Further, all of these hydrogenated forms are very much safer and less noxious than their unsaturated analogues, also as summarized in Table 1.

A wide variety of solvents and solvent mixtures were tested for their effectiveness in replacing xylene (which currently is the standard) both in the preparation steps prior to paraffin wax embedding, and in the dewaxing steps following tissue sectioning. These are the clearing steps that are currently and routinely employed in standard histology practice. The results are shown in Table 1. In addition to the two tests described above, a third test, a paraffin dewaxing test, was also devised in order to provide a more quantitative test. The test results for this third test also are shown in Table 1.

The individual test procedures and the symbols used to describe their results are clearly described in the notes under Table 1.

Examples 1 through 6 clearly demonstrate that the fully-hydrogenated forms of the unsaturated aromatic ring compounds are equal to, or more effective than the unsaturated aromatic ring compounds as clearing solvents themselves. Thus, it is the ring structure, and not the aromaticity, that is important for effective clearing action. This is a completely unexpected result in view of the literature, which teaches that aromatic (unsaturated) solvents are better clearing solvents than are saturated solvents. As the present inventor discovered, saturated ring compounds are actually better than their unsaturated counterparts.

Examples 1 through 6 also show that toxicity and noxiousness can be separated from effectiveness. In fact, these examples clearly show that these effects go in opposite directions. While toxicity and noxiousness were being drastically reduced, the effectiveness as clearing solvents actually increased. Again, this is completely unexpected and is contrary to general knowledge in the clearing solvent art.

Example 7 shows that a broad variety of clearing solvents can be formulated by mixing relatively effective materials like cyclohexane compounds with relatively ineffective carrier solvents like the Micro-Clear TM isoparaffinic petroleum distillate (hereafter "MC-IP"). As shown in the example, the effective range of good clearing solvents would seem to be from 5% to 100% of the effective saturated ring compounds. The formulation of these intermediate clearing solvents allows one to vary dissolving rates, flash points, and other performance factors in a controlled manner. Similarly, many other clearing solvents can be formulated by blending different types of chemicals and petroleum distillates to give a final desired result. In a histological setting, the two end points of primary concern are the rapid and proper removal of alcohol and/or other dehydrants present in gross pieces of tissue prior to paraffin embedding, and the subsequent rapid and effective dewaxing of the tissue slices following microtome sectioning.

TABLE 1

The Comparative Effectiveness, Toxicities and Noxiousness of Various Clearing Agents

| Example # | Clearing Solvent | Activity[a] | Dewax[b] rate | Tox.[c] | Nox.[d] |
|---|---|---|---|---|---|
| 1 | Toluene | 1–2 | 243 | ++++ | ++++ |
|   | Methylcyclohexane | 1 | 216 | + | ++ |
| 2 | Xylene | 1–2 | 402 | ++++ | ++ |
|   | d-Limonene | 3 | 805 | ++++ | ++++ |
|   | Dimethylcyclohexane | 1 | 281 | + | + |
| 3 | Chlorobenzene | 2 | 426 | ++++ | ++++ |
|   | Chlorocyclohexane | 1 | 376 | + | + |
| 4 | Naphthalene[e] | 2[e] | 731[e] | ++++[e] | ++++[e] |
|   | Decahydronaphthalene | 1 | 589 | + | ++ |
| 5 | Quinoline | 2 | >2000 | ++++ | ++++ |
|   | Decahydroquinoline | 1 | 907 | + | ++ |
| 6 | Aromatic Petroleum Distillate | 1–2 | 703 | ++++ | ++++ |
|   | Fully-hydrogenated Petroleum Distillate | 1 | 597 | + | + |
| 7 | Methylcyclohexane (MCH) 100% | 1 | 216 | + | ++ |
|   | 50% MCH + 50% MC-IP | 2 | 426 | + | ++ |
|   | 25% MCH + 75% MC-IP | 3 | 714 | + | + |
|   | 12.5% MCH + 87.5% MC-IP | 4 | 822 | + | + |
|   | 5.0% MCH + 95.0% MC-IP | 5 | 912 | + | + |

TABLE 1-continued

The Comparative Effectiveness, Toxicities and Noxiousness of Various Clearing Agents

| Example # | Clearing Solvent | Activity[a] | Dewax[b] rate | Tox.[c] | Nox.[d] |
|---|---|---|---|---|---|
| | MC-IP 100% | 6 | 953 | + | + |

[a]The comparative Activity or Effectiveness of the indicated clearing solvents in each example was measured in both pre-embedding and dewaxing steps as described in the text. In all cases, the comparative results seen in the pre-embedding step were the same as those seen in the dewaxing step. The best result of each Example was assigned a value of "1", with decreasing numbers assigned for comparatively poorer performances. A value of "1–2" denotes a performance equal to or poorer than "1". This grading system is not used to compare between examples as the tests are not quantitative enough for this purpose. Rather, the rating is used to show the relative performance of the solvents within each example.

[b]Quantitative paraffin dewaxing test. Histology-type paraffin embedding wax (1.0 g portions) was melted in the bottoms of 50 ml Corning ™ glass beakers and allowed to cool to room temperature (21–22° C.) overnight. A 1.0 inch magnetic stirring bar was placed on top of the congealed wax, and the beaker was placed on a magnetic stir motor operating at a standard speed of 600 rpm. At time "zero", 20.0 ml of the clearing solvent being tested was added to the beaker with stirring, and the dissolving process was timed. The timing was stopped when the last of the paraffin in the centermost 90% of the bekaer bottom was no longer visible. In all cases, the corner of the beaker still contained visible wax. The results shown are expressed in seconds.

All experiments were performed in duplicate, and xylene was included in each run as a control. Xylene replicates within each run consistently tested within ± 3–4%; run to run variation was ±8% (due mainly to daily temperature variations).

[c]Human toxicity information was compiled from two sources: The Hazard Material Information System (HMIS; also called the NFPA System) which is a classification system employed by OSHA; and from the Sigma-Aldrich Chemical Safety Data. The symbols used in the Table have the following meanings:

++++, Major health hazards reported, including one or more of the following severe effects: damage to liver, blood, kidneys, eyes or central nervous system.

+, Minor health hazards reported, consisting mainly of irritation of eyes, nose, other mucous membranes, or skin.
[d]Noxious effects were compiled from comparative reports from laboratory workers. The symbols used in the Table have the following meanings:

++++, Overpowering noxious effects, including one or more of the following severe effects: overpowering odor, severe headache, nausea or vomiting; severe coughing or shortness of breath; or sever irritation to eyes, nose, or other mucous membranes.

++, Unpleasant noxious effects, consisting of one or more of the effects noted above, but classified as moderate or tolerable in the degree of intensity of discomfort.

+, Noticeable but not serious levels of discomfort, including drying of the skin
[e]Naphthalene is a solid with limited solubility in even aromatic petroleum solvents. It therefore was necessary to make a solution of the naphthalene in order to test it. The solvent in this case was an aromatic petroleum distillate having a flash point of 148° C.. Only a 20% (weight/volume) solution could be prepared. For comparative purposes, the decahydronaphthalene was similarly prepared as a 20% (w/v) solution. The "effectiveness" and "dewaxing" results shown in the Table are for these 20% solutions; the "toxicity" and "noxiousness" results are for the pure material.

While the invention has been described in detail and with reference to specific embodiments thereof, it will be apparent to one skilled in the art that various changes and modifications can be made therein without departing from the spirit and scope of the invention.

I claim:

1. A method of preparing biological material for microscopic examination, comprising contacting said biological material with a clearing solvent to remove alcohol and/or other dehydrants contained in the biological material or to remove wax contained in the biological material, wherein the clearing solvent consists essentially of from 5% to 100% by weight of a compound or combination of compounds having a higher flashpoint than xylene which is selected from the group consisting of unsubstituted and substituted saturated, organic ring-containing compounds, hydrogenated aromatic petroleum distillates, and combinations thereof.

2. The method of claim 1 wherein the clearing solvent is an organic ring-containing compound selected from the group consisting of unsubstituted and substituted cyclopentane, cyclopentene, cyclohexane and cyclohexene.

3. The method of claim 2 wherein the substituents are selected from the group consisting of straight and branched chain alkyl and alkenyl groups having 1 to 10 carbon atoms and halogen groups.

4. The method of claim 1 wherein the clearing solvent is an organic ring-containing compound selected from the group consisting of cyclopentane, cyclopentene, cyclohexane and cyclohexene which is itself substituted with an organic ring-containing compound selected from the group consisting of unsubstituted and substituted cyclopentane, cyclopentene, cyclohexane and cyclohexene.

5. The method of claim 1 wherein the clearing solvent is an organic ring-containing compound selected from the group consisting of unsubstituted and substituted saturated forms of biphenyl, naphthalene, quinoline, isoquinoline, acenaphthene, and cyclopentadiene.

6. The method of claim 1 wherein the dewaxing agent is an organic ring-containing compound selected from the group consisting of unsubstituted and substituted saturated forms of fluorene, phenanthrene, anthracene, p-terphenyl fluoranthene, pyrene and chrysene.

7. The method of claim 1 wherein the dewaxing agent is an organic ring-containing compound selected from the group consisting of acids derived from the compounds listed in claim 2.

8. The method of claim 7 wherein the dewaxing agent is selected from the group consisting of cyclopentanecarboxylic acid, cyclopentylacetic acid, alkyl-substituted cyclopentyl formic acid, alkyl-substituted cyclopentenyl formic acid, alkyl-substituted cyclohexyl formic acid, alkyl-substituted cyclohexenyl formic acid, alkenyl-substituted cyclopentyl formic acid, alkenyl-substituted cyclopentenyl formic acid, alkenyl-substituted cyclohexyl formic acid, alkenyl-substituted cyclohexenyl formic acid, alkyl-substituted cyclopentyl acetic acid, alkyl-substituted cyclopentenyl acetic acid, alkyl-substituted cyclohexyl acetic acid, alkyl-substituted cyclohexenyl acetic acid, alkenyl-substituted cyclopentyl acetic acid, alkenyl-substituted acid, and alkenyl-substituted cyclohexenyl acetic acid.

9. The method of claim 1 wherein the dewaxing agent is an organic ring-containing compound selected from the group consisting of nitrogen and/or sulfur containing ring compounds.

10. The method of claim 9 wherein the dewaxing agent is selected from the group consisting of unsubstituted and substituted saturated or partially-saturated quinoline, isoquinoline, pyridine, indole, acridine, carbazole, tetramethylene and pentamethylene sulfides.

11. The method of claim 1 wherein the clearing solvent is prepared by distilling a mixture of saturated and unsaturated organic ring-containing compounds and selecting distillation fractions that have higher percentages by weight of saturated organic ring-containing compounds compared to the starting mixture.

* * * * *